United States Patent
Barakat et al.

(10) Patent No.: US 9,822,128 B1
(45) Date of Patent: Nov. 21, 2017

(54) SUBSTITUTED SPIROOXINDOLES

(71) Applicant: KING SAUD UNIVERSITY, Riyadh (SA)

(72) Inventors: Assem Barakat, Riyadh (SA); Mohammad Shahidul Islam, Riyadh (SA); Abdullah Mohammed Al Majid, Riyadh (SA); Hussain Mansur Ghawas, Riyadh (SA); Fardous F. El-Senduny, Mansoura (EG); Farid A. Badria, Mansoura (EG); Yaseen Ali Mosa Mohamed Elshaier, Assuit (EG); Hazem A. Ghabbour, Riyadh (SA)

(*) Notice: Subject to any disclaimer, the term of this patent is extended or adjusted under 35 U.S.C. 154(b) by 0 days.

(21) Appl. No.: 15/611,771

(22) Filed: Jun. 1, 2017

(51) Int. Cl.
*C07D 513/20* (2006.01)

(52) U.S. Cl.
CPC ................... *C07D 513/20* (2013.01)

(58) Field of Classification Search
CPC .................................................. C07D 513/20
See application file for complete search history.

(56) References Cited

U.S. PATENT DOCUMENTS

| 9,486,444 | B1* | 11/2016 | Almansour | .......... A61K 31/435 |
|---|---|---|---|---|
| 2011/0112052 | A1 | 5/2011 | Wang et al. | |
| 2012/0122947 | A1 | 5/2012 | Wang et al. | |
| 2012/0289494 | A1 | 11/2012 | Wang et al. | |
| 2015/0246927 | A1 | 9/2015 | Cui et al. | |
| 2016/0194331 | A1 | 7/2016 | Yamauchi et al. | |

FOREIGN PATENT DOCUMENTS

| CN | 104650096 A | * | 5/2015 |
|---|---|---|---|
| KR | 10-2012-0113109 | | 10/2012 |

* cited by examiner

*Primary Examiner* — Matthew Coughlin
(74) *Attorney, Agent, or Firm* — Richard C. Litman (57) ABSTRACT

The substituted spirooxindoles are MDM2-p53 inhibitors bearing a benzylidine (styryl) arm and have a complex fused ring system ideally suited for binding to the MDM2 protein, thereby interrupting its protein-protein interaction (PPI). Sixteen compounds, designated 4a-4p, were synthesized in a simple smooth method using an asymmetric 1,3-dipolar reaction as the key step. Testing showed that the compounds exhibit anti-cancer activity against various forms of cancer cells affecting humans.

3 Claims, 7 Drawing Sheets

SUBSTITUTED SPIROOXINDOLES

BACKGROUND OF THE INVENTION

1. Field of the Invention

The present invention relates to anti-cancer agents, and particularly to substituted spirooxindoles that inhibit p53-MDM2 interaction.

2. Description of the Related Art

Cancer is a major cause of morbidity and mortality, with approximately 14 million new cases and 8 million cancer-related deaths in 2012, affecting populations in all countries and all regions. These estimates correspond to age-standardized incidence and mortality rates of 182 and 102 per 100 000, respectively.

Much recent cancer research has focused on the p53-MDM2 loop. The p53 protein, often referred to as a tumor suppressor, has been linked to transcription of proteins that mark cancer cells for cell death. Nevertheless, p53 levels that are too high may mark normal cells for cell death. The levels of p53 in a cell are regulated by the protein MDM2. Coincidentally, the expression of MDM2 protein in the cell is the result of activation of the MDM2 gene by p53 itself. The mechanism by which MDM2 regulates p53 levels is related to the conformation of the MDM2 protein, which has folds defining a deep cleft that define a binding site for the N-terminal end of the p53 protein. Actual binding has been linked to four pairs of amino acids in p53 and MDM2 that bond to each other. Uncontrolled growth of cancerous tumors has been correlated with elevated levels of MDM2, leading to over-suppression of p53 in at least some cancers. For example, the overexpression of MDM2 has been observed in a wide range of tumor types, including brain (11%), breast (5-40%), soft tissue tumors (17%).

Consequently, one proposed strategy is to identify pharmaceutical agents that will inhibit p53-MDM2 interaction by selectively binding to the site in the MDM2 protein that normally binds the p53 protein in order to elevate p53 levels. Macromolecules and long chain proteins are not suitable because they cannot fit into the deep cleft where the binding site is located. Hence, the focus has been on small molecules. Several selective small-molecule inhibitors have been previously reported that block the MDM2-p53 protein-protein interaction and activation of p53 as a potential cancer therapeutic strategy. Although some of the inhibitors have been spirooxindole-containing compounds, there is still a need to identify further selective small-molecule inhibitors with anti-cancer activity and other attractive biological activities for pharmacological use in the treatment of cancer.

Thus, substituted spirooxindoles solving the aforementioned problems are desired.

SUMMARY OF THE INVENTION

The substituted spirooxindoles are MDM2-p53 inhibitors bearing a benzylidine (styryl) arm and have a complex fused ring system ideally suited for binding to the MDM2 protein, thereby interrupting its protein-protein interaction (PPI). Sixteen compounds, designated 4a-4p, were synthesized in a simple smooth method using an asymmetric 1,3-dipolar reaction as the key step. Testing showed that the compounds exhibit anti-cancer activity against various forms of cancer cells affecting humans.

Thirteen of the compounds have the following general formula I:

wherein $R_1$ and $R_4$ are independently hydrogen or chlorine; $R_2$ is hydrogen, chlorine, fluorine bromine, trifluoromethyl, methyl, or methoxy; $R_3$ is hydrogen, nitro ($NO_2$), fluorine, or bromine; and $R_5$ is hydrogen, chlorine, or bromine.

Two of the compounds have the following general formula II:

wherein X is sulfur or oxygen.

Finally, a single compound has the following formula III:

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The substituted spirooxindoles are MDM2-p53 inhibitors bearing a benzylidine (styryl) arm and have a complex fused ring system ideally suited for binding to the MDM2 protein, thereby interrupting its protein—protein interaction (PPI). Sixteen compounds, designated 4a-4p, were synthesized in a simple smooth method using an asymmetric 1,3-dipolar reaction as the key step. Testing showed that the compounds exhibit anti-cancer activity against various forms of cancer cells affecting humans.

Thirteen of the compounds have the following general formula I:

wherein $R_1$ and $R_4$ are independently hydrogen or chlorine; $R_2$ is hydrogen, chlorine, fluorine bromine, trifluoromethyl, methyl, or methoxy; $R_3$ is hydrogen, nitro ($NO_2$), fluorine, or bromine; and $R_5$ is hydrogen, chlorine, or bromine.

Two of the compounds have the following general formula II:

wherein X is sulfur or oxygen.

Figure 1:
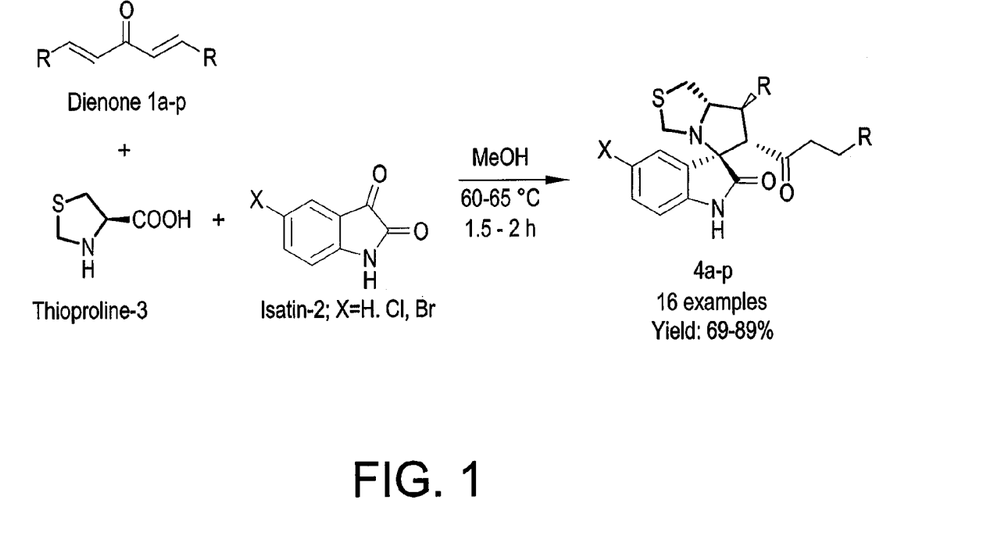
FIG. 1 is a reaction scheme for the synthesis of substituted spirooxindoles according to the present invention.
Figure 2A:
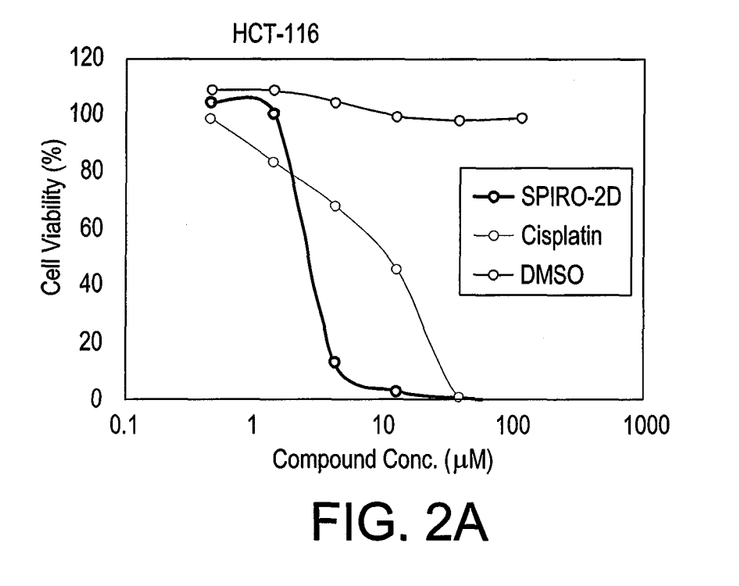
FIG. 2A is a plot of cell viability as a function of concentration comparing the cytotoxic activity against mammalian cancer cell line HCT-116 of compound 4d with cisplatin, DMSO being used as a reference control.
Figure 2B:
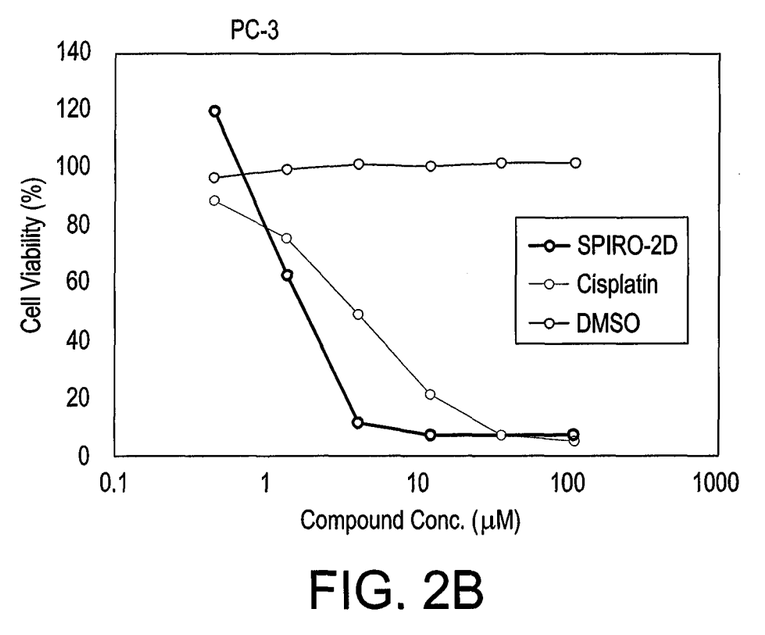
FIG. 2B is a plot of cell viability as a function of concentration comparing the cytotoxic activity against mammalian cancer cell line PC-3 of compound 4d with cisplatin, DMSO being used as a reference control.
Figure 2C:
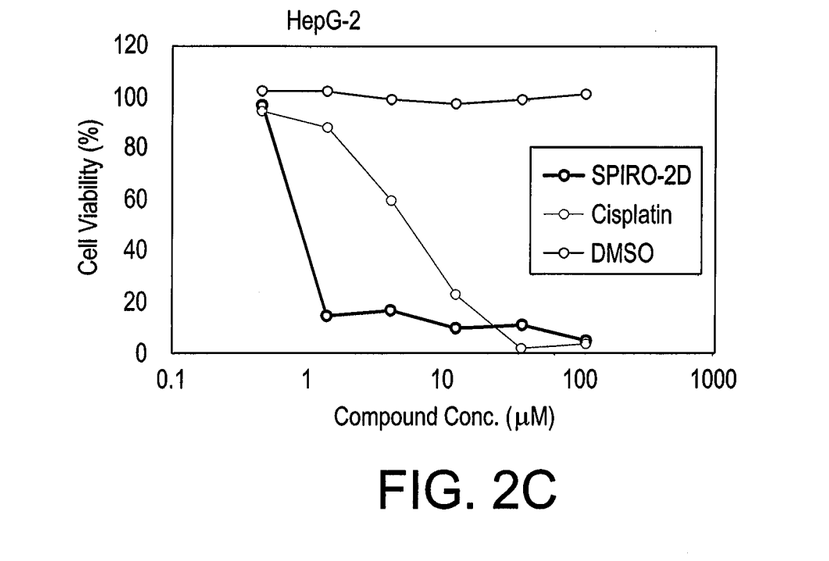
FIG. 2C is a plot of cell viability as a function of concentration comparing the cytotoxic activity against mammalian cancer cell line HepG-2 of compound 4d with cisplatin, DMSO being used as a reference control.

Finally, a single compound has the following formula III:

Our spirooxindole-containing MDM2 inhibitors were synthesized using an efficient 1,3-dipolar cycloaddition reaction, shown in FIG. 1. In our initial endeavor, α,β-unsaturated dienone derivative 1 was prepared by a previously reported method. Then, the one-pot reaction of α,β-unsaturated dienone derivative 1, isatin 2, and L-4-thiazolidinecarboxylic acid 3 was carried out at 60° C. in MeOH for 1.5-2.0 h to afford a compound with 4 stereogeneric centers, designated compound 4a, in 83% yield. The molecular structure of the cycloadduct was confirmed by nuclear magnetic resonance (NMR) spectroscopic analyses. The reaction afforded the adduct 4a as a single regioisomer and with full chemoselectivity. The structures of 4a and its derivatives were deduced by $^1$H-NMR, $^{13}$C-NMR, mass spectrometry (MS), infrared (IR) spectroscopy, elemental analysis, and X-ray crystallography.

The present substituted spirooxindoles will be better understood by reference to the following examples. In the following, all the chemicals were purchased from Aldrich, Sigma-Aldrich, Fluka etc., and were used without further purification, unless otherwise stated. All melting points were measured on a Gallenkamp melting point apparatus in open glass capillaries and are uncorrected. IR Spectra were measured as KBr pellets on a Nicolet 6700 FT-IR spectrophotometer. The NMR spectra were recorded on a Varian Mercury Jeol-400 NMR spectrometer. $^1$H-NMR (400 MHz), and $^{13}$C-NMR (100 MHz) were run in either deuterated dimethylsulphoxide (DMSO-$d_6$) or deuterated chloroform (CDCl$_3$). Chemical shifts (δ) are referred to in terms of ppm, and J-coupling constants are given in Hz. Mass spectra were recorded on a Jeol of JMS-600 H. Elemental analysis was carried out on Elmer 2400 Elemental Analyzer; CHN mode.

Dienones 1a-p (0.5 mmol,) Isatine (74 mg, 0.5 mmol) and thioproline (100 mg, 1.5 mmol) were dissolved in 20 mL of dry MeOH in a 50 mL round bottom flask. The reaction mixture was then heated for 1.5-2 hours at 60-65° C. After the reaction was completed, as monitored by TLC, the crude material was subjected to column chromatography using ethyl acetate/n-hexane (2:3) to give the desired compound 4a-p.

Example 1

Structure and Characterization of Compound 4a

Compound 4a has the chemical name (3R,6'S,7'R,7a'S)-7'-phenyl-6'-((E)-3-(p-tolyl)acryloyl)-1',6',7',7a'-tetrahydro-3'H-spiro[indoline-3,5'-pyrrolo[1,2-c]thiazol]-2-one and the following structural formula:

Yield 194 mg (0.42 mmol, 83.3%); m.p. 94-96° C.; $^1$H-NMR (400 MHz, DMSO-$d_6$) δ: 2.24 (s, 3H, C$\underline{H}_3$), 2.28 (s, 3H, C$\underline{H}_3$), 2.29-3.00 (m, 2H, C$\underline{H}_2$), 3.31 (d, 1H, J=8.76 Hz, C$\underline{H}_2$), 3.71 (t, 1H, J=10.24 Hz, C$\underline{H}_2$), 3.77 (d, 1H, J=9.52 Hz, C$\underline{H}$), 4.00-4.04 (m, 1H, C$\underline{H}$), 4.26 (d, 1H, J=12.44 Hz, C$\underline{H}$), 6.31 (d, 1H, J=16.12 Hz, C$\underline{H}$=CH), 6.69 (d, 1H, J=7.32 Hz, Ar$\underline{H}$), 6.90 (t, 1H, J=8.08 Hz, Ar$\underline{H}$), 7.10 (d, 1H, J=16.12 Hz, CH=C$\underline{H}$), 7.12-7.17 (m, 5H, Ar$\underline{H}$), 7.34 (t, 4H, J=7.32 Hz, Ar$\underline{H}$), 7.44 (d, 1H, J=7.36 Hz, Ar$\underline{H}$), 10.62 (s, 1H, N$\underline{H}$); $^{13}$C NMR (100 MHz, DMSO-$d_6$) δ: 20.56, 20.9, 35.8, 50.0, 53.5, 63.7, 73.4, 74.9, 120.9, 123.2, 124.0, 127.8, 127.9, 128.0, 128.3, 129.3, 129.5, 129.7, 131.2, 136.1, 136.4, 140.8, 142.2, 142.8, 178.6, 194.2; IR (KBr, cm-1) $v_{max}$=3241, 3024, 2919, 1725, 1599, 1469, 1178, 1117, 811, 782; [Anal. Calcd. for C$_{29}$H$_{26}$N$_2$O$_2$S: C, 74.65; H, 5.62; N, 6.00. Found: C, 74.87; H, 5.43; N, 6.11]; LC/MS (ESI, m/z): [M+], found 466.10, C$_{29}$H$_{26}$N$_2$O$_2$S for 466.17.

Example 2

Structure and Characterization of Compound 4b

Compound 4b has the chemical name (3R,6'S,7'R,7a'S)-7'-(p-tolyl)-6'-((E)-3-(p-tolyl)acryloyl)-1',6',7',7a'-tetrahydro-3'H-spiro[indoline-3,5'-pyrrolo[1,2-c]thiazol]-2-one and the following structural formula:

Yield 214 mg (0.44 mmol, 89.1%); m.p. 98-100° C.; $^1$H-NMR (400 MHz, DMSO-$d_6$) δ: 2.24 (s, 3H, C$\underline{H}_3$), 2.28 (s, 3H, C$\underline{H}_3$), 2.97-2.99 (m, 2H, C$\underline{H}_2$), 3.32 (d, 1H, J=10.24 Hz, C$\underline{H}_2$), 3.71 (d, 1H, J=10.24 Hz, C$\underline{H}_2$), 3.73 (t, 1H, J=10.64 Hz, C$\underline{H}$), 3.99-4.03 (m, 1H, C$\underline{H}$), 4.27 (d, 1H, J=11.72 Hz, C$\underline{H}$), 6.31 (d, 1H, J=16.12 Hz, C$\underline{H}$=CH), 6.69 (d, 1H, J=7.32 Hz, Ar$\underline{H}$), 6.90 (t, 1H, J=7.32 Hz, Ar$\underline{H}$), 7.10 (d, 1H, J=16.12 Hz, CH=C$\underline{H}$), 7.12-7.17 (m, 4H, Ar$\underline{H}$), 7.34 (t, 4H, J=7.32 Hz, Ar$\underline{H}$), 7.44 (d, 1H, J=7.36 Hz, Ar$\underline{H}$); 10.62 (s, 1H, N$\underline{H}$); $^{13}$C NMR (100 MHz, DMSO-$d_6$) δ: 20.57, 21.0, 35.8, 50.0, 53.5, 63.7, 73.4, 74.9, 120.9, 123.2, 124.0, 127.8, 127.9, 128.3, 129.3, 129.5, 129.7, 131.2, 136.1, 136.4, 140.8, 142.2, 142.8, 178.6, 194.2; IR (KBr, cm-1) $v_{max}$=3241, 3023, 2918, 1730, 1599, 1469, 1329, 1178, 1117, 811, 750; [Anal. Calcd. for C$_{30}$H$_{28}$N$_2$O$_2$S: C, 74.97; H, 5.87; N, 5.83. Found: C, 75.09; H, 6.03; N, 5.75]; LC/MS (ESI, m/z): [M+], found 480.2, C$_{30}$H$_{28}$N$_2$O$_2$S for 480.19.

Example 3

Structure and Characterization of Compound 4c

Compound 4c has the chemical name (3R,6'S,7'R,7a'S)-7'-(4-chlorophenyl)-6'-((E)-3-(4-chlorophenyl)acryloyl)-1',6',7',7a'-tetrahydro-3'H-spiro[indoline-3,5'-pyrrolo[1,2-c]thiazol]-2-one and the following structural formula:

4c

Yield 198 mg (0.38 mmol, 76.2%); m.p. 99-101° C.; $^1$H-NMR (400 MHz, DMSO-$d_6$) δ: 2.98 (d, 2H, J=4.40 Hz, C$\underline{H}_2$), 3.32 (d, 1H, J=10.24 Hz, C$\underline{H}_2$), 3.70 (d, 1H, J=10.28 Hz, C$\underline{H}_2$), 3.81 (t, 1H, J=10.62 Hz, C$\underline{H}$), 3.98-4.08 (m, 1H, C$\underline{H}$), 4.29 (d, 1H, J=12.48 Hz, C$\underline{H}$), 6.36 (d, 1H, J=16.12 Hz, C$\underline{H}$=CH), 6.69 (d, 1H, J=8.08 Hz, Ar$\underline{H}$), 6.90 (t, 1H, J=7.32 Hz, Ar$\underline{H}$), 7.10-7.16 (m, 2H, Ar$\underline{H}$ & CH=C$\underline{H}$), 7.37-7.47 (m, 8H, Ar$\underline{H}$), 7.52 (d, 2H, J=8.80 Hz, Ar$\underline{H}$); 10.64 (s, 1H, N$\underline{H}$); $^{13}$C NMR (100 MHz, DMSO-$d_6$) δ: 35.7, 49.5, 54.2, 63.9, 73.3, 74.5, 109.7, 121.0, 123.0, 125.3, 128.0, 128.6, 128.9, 129.9, 131.8, 132.8, 135.2, 138.9, 141.8, 142.2, 178.4, 197.3; IR (KBr, cm−1) $v_{max}$=3239, 3057, 2920, 1728, 1612, 1489, 1468, 1327, 1177, 1089, 1012, 819, 749; [Anal. Calcd. for $C_{28}H_{22}Cl_2N_2O_2S$: C, 64.49; H, 4.25; N, 5.37. Found: C, 64.53; H, 4.19; N, 5.46]; LC/MS (ESI, m/z): [M+], found 520.01, $C_{28}H_{22}Cl_2N_2O_2S$ for 520.08.

Example 4

Structure and Characterization of Compound 4d

Compound 4d has the chemical name (3R,6'S,7'R,7a'S)-7'-(2,4-dichlorophenyl)-6'-((E)-3-(2,4-dichlorophenyl)acryloyl)-1',6',7',7a'-tetrahydro-3'H-spiro[indoline-3,5'-pyrrolo[1,2-c]thiazol]-2-one and the following structural formula:

4d

Yield 218 mg (0.37 mmol, 74.1%); m.p. 97-98° C.; $^1$H-NMR (400 MHz, DMSO-$d_6$) δ: 2.92-3.03 (m, 2H, C$\underline{H}_2$), 3.35 (d, 1H, J=9.92 Hz, C$\underline{H}_2$), 3.71 (d, 1H, J=10.24 Hz, C$\underline{H}_2$)), 4.00-4.03 (m, 1H, C$\underline{H}$), 4.13-4.44 (m, 2H, C$\underline{H}$), 6.37 (d, 1H, J=16.12 Hz, C$\underline{H}$=CH), 6.71 (d, 1H, J=7.32 Hz, Ar$\underline{H}$), 6.94 (t, 1H, J=7.68 Hz, Ar$\underline{H}$), 7.13-7.18 (m, 2H, Ar$\underline{H}$ & CH=C$\underline{H}$), 7.35 (d, 1H, J=8.04 Hz, Ar$\underline{H}$), 7.39-7.45 (m, 2H, Ar$\underline{H}$), 7.50 (d, 1H, J=8.80 Hz, Ar$\underline{H}$), 7.63-7.64 (m, 2H, Ar $\underline{H}$); 7.70 (d, 1H, J=8.80 Hz, Ar$\underline{H}$), 10.71 (s, 1H, N$\underline{H}$); $^{13}$C-NMR (100 MHz, DMSO-$d_6$) δ: 35.4, 44.9, 53.7, 64.1, 73.0, 74.7, 109.9, 121.2, 122.8, 127.4, 127.6, 127.9, 129.0, 129.2, 129.5, 130.1, 130.3, 130.7, 132.2, 134.6, 134.8, 135.6, 135.8, 136.0, 142.4, 178.1, 193.9; IR (KBr, cm−1) $v_{max}$=3245, 3059, 2918, 1723, 1315, 1582, 1470, 1384, 1327, 1100, 1074, 790, 751; [Anal. Calcd. for $C_{28}H_{20}Cl_4N_2O_2S$: C, 56.94; H, 3.41; N, 4.75. Found: C, 57.12; H, 3.53; N, 4.83]; LC/MS (ESI, m/z): [M+], found 588.10, $C_{28}H_{20}Cl_4N_2O_2S$ for 588.00.

Example 5

Structure and Characterization of Compound 4e

Compound 4e has the chemical name (3R,6'S,7'R,7a'S)-7'-(2,6-dichlorophenyl)-6'-((E)-3-(2,6-dichlorophenyl)acryloyl)-1',6',7',7a'-tetrahydro-3'H-spiro[indoline-3,5'-pyrrolo[1,2-c]thiazol]-2-one and the following structural formula:

4e

Yield 218 mg (0.37 mmol, 74.1%); m.p. 97-98° C.; $^1$H-NMR (400 MHz, DMSO-$d_6$) δ: 2.92-3.03 (m, 2H, C$\underline{H}_2$), 3.35 (d, 1H, J=9.92 Hz, C$\underline{H}_2$), 3.71 (d, 1H, J=10.24 Hz, C$\underline{H}_2$)), 4.00-4.03 (m, 1H, C$\underline{H}$), 4.13-4.44 (m, 2H, C$\underline{H}$), 6.37 (d, 1H, J=16.12 Hz, C$\underline{H}$=CH), 6.71 (d, 1H, J=7.32 Hz, Ar $\underline{H}$), 6.94 (t, 1H, J=7.68 Hz, Ar$\underline{H}$), 7.13-7.18 (m, 2H, Ar$\underline{H}$ & CH=C$\underline{H}$), 7.35 (d, 1H, J=8.04 Hz, Ar$\underline{H}$), 7.39-7.45 (m, 2H, Ar$\underline{H}$), 7.50 (d, 1H, J=8.80 Hz, Ar$\underline{H}$), 7.63-7.64 (m, 2H, Ar $\underline{H}$); 7.70 (d, 1H, J=8.80 Hz, Ar$\underline{H}$), 10.71 (s, 1H, N$\underline{H}$); $^{13}$C-NMR (100 MHz, DMSO-$d_6$) δ: 35.4, 44.9, 53.7, 64.1, 73.0, 74.7, 109.9, 121.2, 122.8, 127.4, 127.6, 127.9, 129.0, 129.2, 129.5, 130.1, 130.3, 130.7, 132.2, 134.6, 134.8, 135.6, 135.8, 136.0, 142.4, 178.1, 193.9; IR (KBr, cm−1) $v_{max}$=3245, 3059, 2918, 1723, 1315, 1582, 1470, 1384, 1327, 1100, 1074, 790, 751; [Anal. Calcd. for $C_{28}H_{20}Cl_4N_2O_2S$: C, 56.94; H, 3.41; N, 4.75. Found: C, 57.12; H, 3.53; N, 4.83]; LC/MS (ESI, m/z): [M+], found 588.10, $C_{28}H_{20}Cl_4N_2O_2S$ for 588.00.

Example 6

Structure and Characterization of Compound 4f

Compound 4f has the chemical name (3R,6'S,7'R,7a'S)-7'-(4-bromophenyl)-6'-((E)-3-(4-bromophenyl)acryloyl)-1',6',7',7a'-tetrahydro-3'H-spiro[indoline-3,5'-pyrrolo[1,2-c]thiazol]-2-one and the following structural formula:

4f

Yield 214 mg (0.35 mmol, 70.4%); m.p. 203-205° C.; $^1$H-NMR (400 MHz, DMSO-d$_6$) δ: 3.00 (d, 2H, J=5.12 Hz, CH$_2$), 3.33 (d, 1H, J=10.24 Hz, CH$_2$), 3.71 (d, 1H, J=10.28 Hz, CH$_2$)), 3.83 (t, 1H, J=10.66 Hz, CH), 4.00-4.06 (m, 1H, CH), 4.32 (d, 1H, J=11.72 Hz, CH), 6.42 (d, 1H, J=16.12 Hz, CH=CH), 6.70 (d, 1H, J=7.36 Hz, ArH), 6.91 (t, 1H, J=7.32 Hz, ArH), 7.11 (d, 1H, J=16.12 Hz, CH=CH), 7.15 (t, 1H, J=8.08 Hz, ArH), 7.31 (t, 2H, J=8.08 Hz, ArH), 7.45 (t, 3H, J=7.32 Hz, ArH), 7.52 (d, 1H, J=7.32 Hz, ArH), 7.56 (d, 1H, J=7.32 Hz, ArH), 7.70 (d, 2H, J=25.64 Hz, ArH); 10.66 (s, 1H, NH) $^{13}$C NMR (100 MHz, DMSO-d$_6$) δ: 35.5, 49.6, 53.3, 63.3, 73.3, 74.6, 109.7, 121.0, 121.9, 122.2, 123.0, 126.2, 127.1, 127.2, 127.9, 129.9, 130.3, 130.7, 130.8, 130.9, 131.0, 133.1, 136.5, 141.3, 142.2, 142.3, 178.3, 194.4; IR (KBr, cm−1) ν$_{max}$=3083, 3033, 2899, 1712, 1663, 1618, 1586, 1471, 1169, 1009, 983, 817, 748, 541; [Anal. Calcd. for C$_{28}$H$_{22}$Br$_2$N$_2$O$_2$S: C, 55.10; H, 3.63; N, 4.59. Found: C, 54.88; H, 3.47; N, 4.67]; LC/MS (ESI, m/z): [M+], found 608.10, C$_{28}$H$_{22}$Br$_2$N$_2$O$_2$S for 607.98.

Example 7

Structure and Characterization of Compound 4g

Compound 4g has the chemical name (3R,6'S,7'R,7a'S)-7'-(3-nitrophenyl)-6'-(E)-3-(3-nitrophenyl)acryloyl)-1',6',7',7a'-tetrahydro-3'H-spiro[indoline-3,5'-pyrrolo[1,2-c]thiazol]-2-one and the following structural formula:

4g

Yield 198 mg (0.32 mmol, 73.0%); m.p. 112-114° C.; $^1$H-NMR (400 MHz, DMSO-d$_6$) δ: 2.96-2.99 (m, 2H, CH$_2$), 3.31 (d, 1H, J=11.00 Hz, CH$_2$), 3.70-3.72 (m, 2H, CH$_2$)), 3.98-4.06 (m, 1H, CH), 4.21 (d, 1H, J=11.00 Hz, CH), 6.24 (d, 1H, J=16.12 Hz, CH=CH), 6.69 (d, 1H, J=7.32 Hz, ArH), 6.89 (t, 6H, J=8.80 Hz, ArH), 7.09-7.13 (m, 2H, ArH & CH=CH), 7.39 (t, 3H, J=10.28 Hz, ArH), 7.45 (d, 1H, J=8.04 Hz, ArH), 10.60 (s, 1H, NH); $^{13}$C NMR (100 MHz, DMSO-d$_6$) δ: 35.9, 49.7, 53.6, 63.6, 73.5, 74.8, 109.5, 120.8, 122.7, 123.2, 126.4, 127.9, 128.9, 129.6, 130.2, 131.2, 142.1, 142.7, 158.2, 161.4, 178.5, 194.01; IR (KBr, cm−1) ν$_{max}$=3195, 3084, 2922, 1734, 1656, 1615, 1529, 1470, 1351, 1180, 731, 681; [Anal. Calcd. for C$_{28}$H$_{22}$N$_4$O$_6$S: C, 61.98; H, 4.09; N, 10.33. Found: C, 62.14; H, 4.17; N, 10.22]; LC/MS (ESI, m/z): [M+], found 642.10, C$_{28}$H$_{22}$N$_4$O$_6$S for 542.13.

Example 8

Structure and Characterization of Compound 4h

Compound 4h has the chemical name (3R,6'S,7'R,7a'S)-7'-(4-methoxyphenyl)-6'-((E)-3-(4-methoxyphenyl)acryloyl)-1',6',7',7a'-tetrahydro-3'H-spiro[indoline-3,5'-pyrrolo[1,2-c]thiazol]-2-one and the following structural formula:

4h

Yield 210 mg (0.41 mmol, 82.0%); m.p. 92-93° C.; $^1$H-NMR (400 MHz, DMSO-d$_6$) δ: 2.98-3.09 (m, 2H, CH$_2$), 3.35 (d, 1H, J=12.42 Hz, CH$_2$), 3.73 (d, 1H, J=10.28 Hz, CH$_2$)), 4.01 (t, 1H, J=11.72 Hz, CH), 4.12-4.17 (m, 1H, CH), 4.45 (d, 1H, J=11.72 Hz, CH), 6.54 (d, 1H, J=16.88 Hz, CH=CH), 6.69 (d, 1H, J=7.32 Hz, ArH), 6.93 (t, 1H, J=7.32 Hz, ArH), 7.16 (t, 1H, J=7.36 Hz, ArH), 7.25 (d, 1H, J=16.88 Hz, CH=CH), 7.51 (d, 1H, J=7.32 Hz, ArH), 7.63-7.67 (m, 2H, ArH), 7.88 (d, 1H, J=8.04 Hz, ArH), 8.02 (d, 1H, J=7.36 Hz, ArH), 8.10 (d, 1H, J=8.04 Hz, ArH), 8.20 (d, 1H, J=8.80 Hz, ArH), 8.25 (s, 1H, ArH), 8.39 (s, 1H, ArH); 10.69 (s, 1H, NH); $^{13}$C NMR (100 MHz, DMSO-d$_6$) δ: 35.5, 49.4, 53.3, 64.2, 73.3, 74.5, 109.8, 121.1, 122.2, 122.8, 122.9, 123.2, 124.8, 127.2, 127.9, 130.0, 130.2, 130.4, 133.9, 135.0, 135.8, 140.5, 141.7, 142.2, 148.0, 148.2, 178.2, 194.5; IR (KBr, cm−1) ν$_{max}$=3241, 2925, 2835, 1730, 1595, 1511, 1467, 1252, 1173, 1115, 1030, 827, 750; [Anal. Calcd. for C$_{30}$H$_{28}$N$_2$O$_4$S: C, 70.29; H, 5.51; N, 5.46. Found: C, 70.01; H, 5.37; N, 5.32]; LC/MS (ESI, m/z): [M+], found 512.20, C$_{30}$H$_{28}$N$_2$O$_4$S for 512.18.

Example 9

Structure and Characterization of Compound 4i

Compound 4i has the chemical name (3R,6'S,7'R,7a'S)-7'-(naphthalen-2-yl)-6'-((E)-3-(naphthalen-2-yl)acryloyl)-1',6',7',7a'-tetrahydro-3'H-spiro[indoline-3,5'-pyrrolo[1,2-c]thiazol]-2-one and the following structural formula:

4i

Yield 191 mg (0.35 mmol, 69.2%); m.p. 210-212° C.; $^1$H-NMR (400 MHz, DMSO-$d_6$) δ: 2.85-3.10 (m, 2H, C$\underline{H}_2$), 3.46 (d, 1H, J=10.24 Hz, C$\underline{H}_2$), 3.80 (d, 1H, J=10.24 Hz, C$\underline{H}_2$)), 4.23 (s, 1H, C$\underline{H}$), 4.73-4.85 (m, 2H, C$\underline{H}$), 6.33 (d, 1H, J=16.12 Hz, C$\underline{H}$=CH), 6.74 (d, 1H, J=7.32 Hz, Ar$\underline{H}$), 7.05 (t, 1H, J=8.04 Hz, Ar$\underline{H}$), 7.21 (t, 1H, J=8.04 Hz, Ar$\underline{H}$), 7.43 (t, 1H, J=8.04 Hz, CH=C$\underline{H}$), 7.52-7.64 (m, 6H, Ar$\underline{H}$& CH=C$\underline{H}$), 7.71 (t, 1H, J=7.36 Hz, Ar$\underline{H}$), 7.83-7.96 (m, 6H, Ar$\underline{H}$), 8.05 (d, 1H, J=8.04 Hz, Ar$\underline{H}$), 8.57 (d, 1H, J=8.80 Hz, Ar$\underline{H}$), 10.74 (s, 1H, N$\underline{H}$); $^{13}$C NMR (100 MHz, DMSO-$d_6$) δ: 36.1, 49.5, 53.7, 64.1, 73.8, 74.7, 110.0, 121.4, 123.1, 123.2, 123.4, 125.1, 125.5, 125.7, 126.4, 127.2, 127.8, 128.0, 128.6, 128.8, 129.9, 130.3, 130.7, 131.0, 131.2, 131.9, 132.1, 133.0, 133.8, 135.9, 139.5, 142.3, 178.7, 194.6; IR (KBr, cm−1) $v_{max}$ 3243, 2927, 2839, 1738, 1591, 1514, 1469, 1257, 1178, 1119, 1036, 827, 750, 508, 431; [Anal. Calcd. for $C_{36}H_{28}N_2O_2S$: C, 78.23; H, 5.11; N, 5.07. Found: C, 78.35; H, 5.27; N, 5.18]; LC/MS (ESI, m/z): [M+], found 552.20, $C_{36}H_{28}N_2O_2S$ for 552.19.

Example 10

Structure and Characterization of Compound 4j

Compound 4j has the chemical name (3R,6'S,7'S,7a'S)-7'-(thiophen-2-yl)-6'-((E)-3-(thiophen-2-yl)acryloyl)-1',6',7',7a'-tetrahydro-3'H-spiro[indoline-3,5'-pyrrolo[1,2-c]thiazol]-2-one and the following structural formula:

4j

Yield 176 mg (0.38 mmol, 75.8%); m.p. 83-85° C.; $^1$H-NMR (400 MHz, DMSO-$d_6$) δ: 2.99 (d, 2H, J=4.36 Hz, C$\underline{H}_2$), 3.32 (d, 1H, J=8.04 Hz, C$\underline{H}_2$), 3.71 (d, 1H, J=10.24 Hz, C$\underline{H}$)), 3.82 (t, 1H, J=10.64 Hz, C$\underline{H}$), 4.03 (q, 1H, J=4.40 Hz, C$\underline{H}$), 4.29 (d, 1H, J=12.48 Hz, C$\underline{H}$), 6.32 (d, 1H, J=16.12 Hz, C$\underline{H}$=CH), 6.69 (d, 1H, J=7.36 Hz, Ar$\underline{H}$), 6.90 (t, 1H, J=7.32 Hz, Ar$\underline{H}$), 7.13-7.22 (m, 5H, Ar$\underline{H}$& CH=C$\underline{H}$), 7.44-7.54 (m, 4H, Ar$\underline{H}$), 10.63 (s, 1H, N$\underline{H}$); $^{13}$C NMR (100 MHz, DMSO-$d_6$) δ: 35.6, 49.4, 53.5, 63.8, 73.3, 74.7, 109.7, 115.3, 115.5, 115.9, 116.1, 120.9, 123.1, 124.8, 127.9, 129.8, 129.9, 130.5, 130.7, 135.5, 141.8, 142.2, 178.4, 194.2; IR (KBr, cm-1) $v_{max}$=3239, 3090, 2918, 1731, 1613, 1589, 1468, 1230, 1176, 1117, 750, 703, 588; [Anal. Calcd. for $C_{24}H_{20}N_2O_2S_3$: C, 62.04; H, 4.34; N, 6.03. Found: C, 61.87; H, 4.19; N, 5.95]; LC/MS (ESI, m/z): [M+], found 464.10, $C_{24}H_{20}N_2O_2S_3$ for 464.07.

Example 11

Structure and Characterization of Compound 4k

Compound 4k has the chemical name (3R,6'S,7'S,7a'S)-7'-(furan-2-yl)-6'-((E)-3-(furan-2-yl)acryloyl)-1',6',7',7a'-tetrahydro-3'H-spiro[indoline-3,5'-pyrrolo[1,2-c]thiazol]-2-one and the following structural formula:

4k

Yield 183 mg (0.42 mmol, 84.7%); m.p. 171-173° C.; $^1$H-NMR (400 MHz, DMSO-$d_6$) δ: 3.11-3.12 (m, 2H, C$\underline{H}_2$), 3.30 (d, 1H, J=10.24 Hz, C$\underline{H}_2$), 3.70 (d, 1H, J=10.28 Hz, C$\underline{H}_2$)), 3.88 (t, 1H, J=11.00 Hz, C$\underline{H}$), 4.02 (m, 1H, C$\underline{H}$), 4.19 (d, 1H, J=11.76 Hz, C$\underline{H}$), 6.14 (d, 1H, J=16.12 Hz, C$\underline{H}$=CH), 6.36-6.38 (m, 2H, Ar$\underline{H}$), 6.59-6.60 (m, 1H, Ar$\underline{H}$), 6.75 (d, 1H, J=8.08 Hz, Ar$\underline{H}$), 6.88 (d, 1H, J=3.68 Hz, Ar$\underline{H}$), 6.91 (d, 1H, J=7.32 Hz, Ar$\underline{H}$), 7.99 (d, 1H, J=16.12 Hz, CH=C$\underline{H}$), 7.17 (t, 1H, J=7.32 Hz, Ar$\underline{H}$), 7.35 (d, 1H, J=7.32 Hz, Ar$\underline{H}$), 7.58 (d, 1H, J=1.48 Hz, Ar$\underline{H}$), 7.81 (d, 1H, J=1.48 Hz, Ar$\underline{H}$), 10.69 (s, 1H, N$\underline{H}$); $^{13}$C NMR (100 MHz, DMSO-$d_6$) δ: 36.3, 44.1, 53.7, 61.2, 72.0, 73.3, 106.6, 109.8, 110.5, 113.2, 117.7, 120.9, 121.0, 122.9, 127.9, 129.5, 129.9, 142.2, 142.4, 146.5, 150.0, 152.5, 178.3, 193.0; IR (KBr, cm-1) $v_{max}$=3200, 3091, 2906, 1721, 1609, 1470, 1335, 1173, 1014, 734; [Anal. Calcd. for $C_{24}H_{20}N_2O_4S$: C, 66.65; H, 4.66; N, 6.48. Found: C, 66.43; H, 4.76; N, 6.52]; LC/MS (ESI, m/z): [M+], found 432.10, $C_{24}H_{20}N_2O_4S$ for 432.11.

Example 12

Structure and Characterization of Compound 4l

Compound 4l has the chemical name (3R,6'S,7'R,7a'S)-7'-(3-bromophenyl)-6'-((E)-3-(3-bromophenyl)acryloyl)-1',6',7',7a'-tetrahydro-3'H-spiro[indoline-3,5'-pyrrolo[1,2-c]thiazol]-2-one and the following structural formula:

Yield 216 mg (0.36 mmol, 71.0%); m.p. 88-90° C.; $^1$H-NMR (400 MHz, DMSO-d$_6$) δ: 3.09 (d, 2H, J=2.92 Hz, CH$_2$), 3.30 (d, 1H, J=10.44 Hz, CH$_2$), 3.72 (d, 1H, J=10.24 Hz, CH$_2$)), 4.00-4.12 (m, 3H, CH), 6.10 (d, 1H, J=16.12 Hz, CH=CH), 6.72 (d, 1H, J=8.08 Hz, ArH), 6.90 (t, 1H, J=7.36 Hz, ArH), 6.98 (t, 1H, J=3.68 Hz, ArH), 7.09 (t, 1H, J=4.40 Hz, ArH), 7.14 (m, 2H, ArH), 7.33 (d, 1H, J=16.12 Hz, CH=CH), 7.39-7.40 (m, 5H, ArH), 7.70 (d, 1H, J=4.40 Hz, ArH); 10.68 (s, 1H, NH) $^{13}$C NMR (100 MHz, DMSO-d$_6$) δ: 35.9, 45.5, 53.7, 64.5, 73.5, 74.8, 109.7, 120.9, 121.2, 122.9, 124.0, 124.5, 125.5, 126.6, 127.2, 127.9, 128.8, 129.9, 130.68, 132.1, 133.1, 135.8, 138.8, 141.4, 142.1, 142.3, 178.2, 193.1; IR (KBr, cm−1) ν$_{max}$=3237, 3056, 2919, 1729, 1613, 1562, 1325, 1176, 1071, 978, 777, 749, 685; [Anal. Calcd. for C$_{28}$H$_{22}$Br$_2$N$_2$O$_2$S: C, 55.10; H, 3.63; N, 4.59. Found: C, 55.17; H, 3.58; N, 4.68]; LC/MS (ESI, m/z): [M+], found 608.00, C$_{28}$H$_{22}$Br$_2$N$_2$O$_2$S for 607.98.

Example 13

Structure and Characterization of Compound 4m

Compound 4m has the chemical name (3R,6'S,7'R,7a'S)-7'-(4-fluorophenyl)-6'-((E)-3-(4-fluorophenyl)acryloyl)-1',6',7',7a'-tetrahydro-3'H-spiro[indoline-3,5'-pyrrolo[1,2-c]thiazol]-2-one and the following structural formula:

Yield 183 mg (0.38 mmol, 75.0%); m.p. 195-197° C.; $^1$H-NMR (400 MHz, DMSO-d$_6$) δ: 2.98 (d, 2H, J=5.12 Hz, CH$_2$), 3.31 (d, 1H, J=10.24 Hz, CH$_2$), 3.70 (d, 1H, J=10.28 Hz, CH$_2$)), 3.79 (t, 1H, J=10.66 Hz, CH), 4.00-4.03 (m, 1H, CH), 4.28 (d, 1H, J=11.72 Hz, CH), 6.34 (d, 1H, J=16.12 Hz, CH=CH), 6.69 (d, 1H, J=7.32 Hz, ArH), 6.90 (t, 1H, J=8.08 Hz, ArH), 7.09 (d, 1H, J=16.12 Hz, CH=CH), 7.146 (d, 1H, J=8.04 Hz, ArH), 7.38 (d, 2H, J=8.08 Hz, ArH), 7.44 (t, 3H, J=8.76 Hz, ArH), 7.51-7.56 (m, 4H, ArH), 10.63 (s, 1H, NH); $^{13}$C NMR (100 MHz, DMSO-d$_6$) (δ: 35.5, 49.6, 53.5, 63.8, 73.3, 74.5, 109.7, 120.2, 121.0, 123.0, 124.1, 125.4, 127.8, 130.1, 130.3, 131.5, 131.9, 133.2, 138.8, 140.4, 141.7, 142.2, 178.3, 194.3; IR (KBr, cm−1) ν$_{max}$=3193, 3065, 2909, 1719, 1691, 1616, 1594, 1507, 1469, 1413, 1330, 1227, 1161, 1030, 959, 832, 791, 749, 681, 518; [Anal. Calcd. for C$_{28}$H$_{22}$F$_2$N$_2$O$_2$S: C, 68.84; H, 4.54; N, 5.73. Found: C, 69.01; H, 4.41; N, 5.82]; LC/MS (ESI, m/z): [M+], found 488.10, C$_{28}$H$_{22}$F$_2$N$_2$O$_2$S for 488.14.

Example 14

Structure and Characterization of Compound 4n

Compound 4n has the chemical name (3R,6'S,7'R,7a'S)-7'-(4-(trifluoromethyl)phenyl)-6'-((E)-3-(4-(trifluoromethyl)phenyl)acryloyl)-1',6',7',7a'-tetrahydro-3'H-spiro[indoline-3,5'-pyrrolo[1,2-c]thiazol]-2-one and the following structural formula:

Yield 217 mg (0.37 mmol, 73.8%); m.p. xx ° C.; $^1$H-NMR (400 MHz, DMSO-d$_6$) δ: 2.93 (d, 1H, J=11.72 Hz, CH$_2$), 3.03-3.08 (m, 1H, CH$_2$), 3.54 (d, 1H, J=11.00 Hz, CH), 3.89-3.97 (m, 2H, CH$_2$), 4.32 (d, 1H, J=11.72 Hz, CH), 4.42-4.50 (m, H, CH), 6.21 (d, 1H, J=16.16 Hz, CH=CH), 6.78 (d, 1H, J=7.32 Hz, ArH), 7.00 (t, 1H, J=7.32 Hz, ArH), 7.08 (d, 1H, J=16.16 Hz, CH=CH), 7.15-7.19 (m, 2H, Ar H), 7.31 (d, 2H, J=8.04 Hz, ArH), 7.46 (d, 2H, J=8.04 Hz, ArH), 7.50-7.59 (m, 4H, ArH), 8.59 (s, 1H, NH); $^{13}$C NMR (100 MHz, DMSO-d$_6$) δ: 35.4, 49.7, 53.5, 63.9, 73.4, 74.6, 109.8, 120.1, 121.1, 123.2, 124.2, 125.5, 125.9, 127.9, 130.2, 130.4, 131.6, 131.9, 133.3, 138.9, 140.5, 141.8, 142.3, 178.4, 194.3; IR (KBr, cm−1) ν$_{max}$=3252, 2924, 2854, 1728, 1617, 1470, 1326, 1168, 1123, 1066, 1016, 829, 751; [Anal. Calcd. for C$_{30}$H$_{22}$F6N$_2$O$_2$S: C, 61.22; H, 3.77; N, 4.76. Found: C, 61.33; H, 3.59; N, 4.81]; LC/MS (ESI, m/z): [M+], found 588.10, C$_{30}$H$_{22}$F6N$_2$O$_2$S for 588.13.

Example 15

Structure and Characterization of Compound 4o

Compound 4o has the chemical name (3R,6'S,7'R,7a'S)-5-chloro-7'-(4-fluorophenyl)-6'-((E)-3-(4-fluorophenyl)acryloyl)-1',6',7',7a'-tetrahydro-3'H-spiro[indoline-3,5'-pyrrolo[1,2-c]thiazol]-2-one and the following structural formula:

Yield 206 mg (0.40 mmol, 78.9%); m.p. 81-82° C.; $^1$H-NMR (400 MHz, DMSO-d$_6$) δ: 2.99-3.07 (m, 2H, C$\underline{H}_2$), 3.35 (d, 1H, J=10.28 Hz, C$\underline{H}_2$), 3.72 (d, 1H, J=11.00 Hz, C$\underline{H}_2$)), 3.81 (t, 1H, J=10.26 Hz, C$\underline{H}$), 4.00-4.05 (m, 1H, C$\underline{H}$), 4.32 (d, 1H, J=11.72 Hz, C$\underline{H}$), 6.42 (d, 1H, J=16.16 Hz, C$\underline{H}$=CH), 6.72 (d, 1H, J=8.08 Hz, Ar$\underline{H}$), 6.12-7.24 (m, 6H, Ar$\underline{H}$ & CH=C$\underline{H}$), 7.55-7.58 (m, 5H, Ar$\underline{H}$), 10.77 (s, 1H, N$\underline{H}$); $^{13}$C NMR (100 MHz, DMSO-d$_6$) δ: 35.6, 49.5, 53.8, 63.5, 73.7, 74.7, 111.1, (115.3 & 115.5, $J_{C2\text{-}F}$=21.41 Hz), (115.8 & 116.1, $J_{C2\text{-}F}$=22.18 Hz), 124.7, 125.0, 125.1, 127.9, 129.8, (129.9 & 130.0, $J_{C3\text{-}F}$=8.41 Hz), (130.50 & 130.53, $J_{C4\text{-}F}$=3.06 Hz), (130.7 & 130.8, $J_{C3\text{-}F}$=9.18 Hz), (135.14 & 135.17, $J_{C4\text{-}F}$=3.06 Hz), 141.1, 142.3, (160.1 & 162.2, $J_{C1\text{-}F}$=214.1 Hz), (162.5 & 221.0, $J_{C1\text{-}F}$=221.0 Hz), 178.0, 194.2; IR (KBr, cm−1) $\nu_{max}$=3239, 2922, 1733, 1595, 1509, 1473, 1231, 1159, 828; [Anal. Calcd. for C$_{28}$H$_{21}$ClF$_2$N$_2$O$_2$S: C, 64.30; H, 4.05; N, 5.36. Found: C, 64.19; H, 3.93; N, 5.46]; LC/MS (ESI, m/z): [M+], found 522.10, C$_{28}$H$_{21}$ClF$_2$N$_2$O$_2$S for 522.10.

Example 16

Structure and Characterization of Compound 4p

Compound 4p has the chemical name (3R,6'S,7'R,7a'S)-5-bromo-7'-(4-fluorophenyl)-6'-((E)-3-(4-fluorophenyl)acryloyl)-1',6',7',7a'-tetrahydro-3'H-spiro[indoline-3,5'-pyrrolo[1,2-c]thiazol]-2-one and the following structural formula:

4p

Yield 219 mg (0.38 mmol, 77.4%); m.p. 105-107° C.; $^1$H-NMR (400 MHz, DMSO-d$_6$) δ: 2.97-3.07 (m, 2H, C$\underline{H}_2$), 3.35 (d, 1H, J=10.24 Hz, C$\underline{H}_2$), 3.72 (d, 1H, J=10.76 Hz, C$\underline{H}_2$)), 3.80 (t, 1H, J=10.28 Hz, C$\underline{H}$), 4.01-4.05 (m, 1H, C$\underline{H}$), 4.31 (d, 1H, J=11.72 Hz, C$\underline{H}$), 6.43 (d, 1H, J=16.12 Hz, C$\underline{H}$=CH), 6.69 (d, 1H, J=7.36 Hz, Ar$\underline{H}$), 6.12-7.24 (m, 5H, Ar$\underline{H}$ & CH=C$\underline{H}$), 7.35 (d, 1H, J=8.80 Hz, Ar$\underline{H}$), 7.51-7.58 (m, 4H, Ar$\underline{H}$), 7.68 (1, 1H, Ar$\underline{H}$), 10.79 (s, 1H, N$\underline{H}$); $^{13}$C NMR (100 MHz, DMSO-d$_6$) δ: 35.7, 49.5, 53.9, 63.6, 73.7, 74.7, 111.6, 112.9, (115.3 & 115.5, $J_{C2\text{-}F}$=21.41 Hz), (115.8 & 116.1, $J_{C2\text{-}F}$=22.18 Hz), 124.7, 125.4, (129.9 & 130.0, $J_{C3\text{-}F}$=8.41 Hz), (130.49 & 130.52, $J_{C4\text{-}F}$=3.06 Hz), 130.6, (130.8 & 130.9, $J_{C3\text{-}F}$=9.18 Hz), 132.6, (135.11 & 135.14, $J_{C4\text{-}F}$=3.06 Hz), 141.5, 142.3, (160.1 & 162.2, $J_{C1\text{-}F}$=214.1 Hz), (162.5 & 164.7, $J_{C1\text{-}F}$=221.0 Hz), 177.9, 194.2; IR (KBr, cm−1) $\nu_{max}$=3244, 2920, 17341613, 1597, 1509, 1471, 1232, 1158, 829; [Anal. Calcd. for C$_{28}$H$_{22}$BrF$_2$N$_2$O$_2$S: C, 59.27; H, 3.73; N, 4.94. Found: C, 59.12; H, 3.61; N, 5.11]; LC/MS (ESI, m/z): [M+], found 566.10, C$_{28}$H$_{22}$BrF$_2$N$_2$O$_2$S for 566.05.

Example 17

Antitumor Activity Testing

The cytotoxic activity of the compounds was tested against different mammalian cancer cells, prostate carcinoma cells (PC-3), hepatocellular carcinoma (HepG2) and colon cancer cells (HCT-116) and against African green monkey kidney cell line (Vero-B). The cell lines were obtained from American Type Culture Collection (ATCC). The cells were cultivated at 37° C. and 10% CO$_2$ in DMEM (Lonza, 12-604F) medium supplemented with 10% fetal bovine serum (FBS, Lonza, Cat. No. 14-801E), 100 IU/ml penicillin and 100 µg/ml streptomycin (Lonza, 17-602E). Cisplatin (cis-diamineplatinum (II) dichloride) was used as a positive control and was obtained from Sigma then dissolved in 0.9% saline then stored as 8 mM stock solution at −20° C. The synthesized compounds were solubilized in DMSO and stored at −20° C. 0.5% crystal violet was prepared in Methanol and was used to stain the viable cells (Feoktistova, Geserick et al. 2016). Crystal violet binds to proteins and DNA in the adherent and viable cells so the stain is an indicator for the viability of the treated cells. The viability of the cells were quantified by using MTT reagent (3-(4,5-dimethylthiazol-2-yl)-2,5-diphenyl tetrazolium bromide), which measure the activity of mitochondrial dehydrogenase in the viable cells (Slater, Sawyer et al. 1963, Mosmann 1983).

Cytotoxicity was further assayed as follows. The cells were seeded in 96-well plate as 5*10$^4$ cells/mL (100 µL/well). A serial dilutions of tested compounds or cisplatin (100, 30, 10, 3.3, 1.1 or 0.37 µM) was added after overnight incubation of the cells at 37° C. and 5% CO$_2$. DMSO was used as a control (0.1%). The cells were incubated for 48 hrs. After that, 15 µl of MTT (5 mg/mL PBS) was added to each well and incubated for another 4 hours. The formazan crystals were solubilized by 100 µL acidified SDS solution (10% SDS/0.01 M HCl). The absorbance was measured after 14 hours of incubation at 37° C. and 5% CO$_2$ at 570 nm by Biotech plate reader. Each experiment was repeated three times and standard deviation was calculated (±). IC50% was calculated as the concentration that cause 50% inhibition for cell growth. The growth of the cells were monitored and the images were acquired by Gx microscopes (GXMGXD202 Inverted Microscope) (10× Eyepiece) after staining with crystal violet.

The Selectivity Index (SI) was calculated from the following:

$$SI = \frac{(IC50)\text{normal}}{(IC50)\text{cancer}}$$

where $IC_{50}$ normal=the concentration of the tested compound that killed 50% of normal cells; $IC_{50}$ cancer=the concentration of the same tested compound that killed 50% of cancer cells.

The antitumor activity of the synthesized compounds (16 compounds) was tested against different cancer cells (HCT-116, PC-3 and HepG-2). The data showed that the 16 compounds have anticancer activity against the colon cancer, while 13 compounds have anticancer activity against HepG-2, and only 8 compounds were active against prostate cancer in comparison to the standard chemotherapeutic drug cisplatin. All active compounds showed $IC_{50}\%$ lower than 10 μM, except compound 4j and compound 4k with colon cancer cells. The active compounds against HepG-2 or PC-3, were also active, with $IC_{50}\%$ less than or equal to 0.5 μM, in comparison to cisplatin. The selectivity of the active compound towards the cancer cells versus the normal cells was further studied by testing their antigrowth activity to the epithelial cells from African green monkey (Vero-B). Out of the 16 compounds active against colon cancer, only compounds 4c and 4d were highly selective (SI>2) (HCT-116). On the other hand, the 13 compounds active against hepatocellular carcinoma all showed a selectivity index (SI) higher than 2. The selectivity index of all compounds active against prostate cancer was greater than 2 as well.

TABLE 1

Cytotoxic Activity Against Colon Cancer Cells (HCT-116)

| Compound | HCT-116 ($IC_{50\%}$ μM) | HCT-116 ($IC_{50\%}$ μg/ml) | VERO-B ($IC_{50\%}$ μM) | SI |
|---|---|---|---|---|
| 4a | 9 ± 1 | 4.2 | 8 | 0.888889 |
| 4b | 8 ± 1.2 | 3.8 | 11.8 | 1.475 |
| 4c | 3 ± 0.5 | 1.6 | 7 | 2.333333 |
| 4d | 1.4 ± 0.6 | 0.8 | 5 | 3.571429 |
| 4e | 3 ± 0.3 | 1.8 | 3 | 1 |
| 4f | 3 ± 0.5 | 1.8 | 3 | 1 |
| 4g | 2.5 ± 0.2 | 1.4 | 2.5 | 1 |
| 4h | 7 ± 0.9 | 3.6 | 7.5 | 1.071429 |
| 4i | 8 ± 0.3 | 4.4. | 7 | 0.875 |
| 4j | 14.5 ± 1.5 | 6.7 | 18 | 1.241379 |
| 4k | 19 ± 2 | 10.1 | 25 | 1.315789 |
| 4l | 1.57 ± 0.3 | 0.95 | 3 | 1.910828 |
| 4m | 5 ± 0.3 | 2.4 | 6 | 1.2 |
| 4n | 2.9 ± 0.4 | 1.7 | 2.5 | 0.862069 |
| 4o | 7 ± 0.6 | 3.7 | 8 | 1.142857 |
| 4p | 3.5 ± 0.3 | 2 | 3 | 0.957143 |
| Cisplatin | 12.6 ± 2 | 3.8 | 5 | 0.396825 |

TABLE 2

Cytotoxic Activity Against Hepatocellular Cancer Cells (HepG2)

| Compound | HepG2 ($IC_{50\%}$ μM) | HepG2 ($IC_{50\%}$ μg/ml) | VERO-B ($IC_{50\%}$ μM) | SI |
|---|---|---|---|---|
| 4a | 3.85 ± 0.3 | 1.8 | 8 | 2.0779221 |
| 4b | 3.57 ± 0.5 | 1.7 | 11.8 | 3.3053221 |
| 4c | 2.0 ± 0.5 | 1 | 7 | 3.5 |
| 4d | 0.85 ± 0.2 | 0.5 | 5 | 5.8823529 |
| 4e | 1.0 ± 0.3 | 0.6 | 3 | 3 |
| 4f | 0.8 ± 0.1 | 0.5 | 3 | 3.75 |
| 4h | 2.25 ± 0.2 | 1.1 | 7.5 | 3.3333333 |
| 4i | 2.4 ± 1.0 | 1.3 | 7 | 2.9166667 |
| 4l | 0.9 ± 0.1 | 0.5 | 3 | 3.3333333 |
| 4m | 2.4 ± 0.4 | 1.2 | 6 | 2.5 |
| 4n | 0.9 ± 0.2 | 0.5 | 2.5 | 2.7777778 |
| 4o | 2 ± 0.4 | 1 | 8 | 4 |
| 4p | 0.8 ± 0.1 | 0.5 | 3 | 3.75 |
| Cisplatin | 5.5 ± 1 | 1.7 | 5 | 0.9090909 |

TABLE 3

Cytotoxic Activity Against Prostate Cancer Cell Line

| Compound | PC-3 ($IC_{50\%}$ μM) | PC-3 ($IC_{50\%}$ μg/ml) | VERO-B ($IC_{50\%}$ μM) | SI |
|---|---|---|---|---|
| 4c | 2.7 ± 0.4 | 1.4 | 7 | 2.592593 |
| 4d | 1.8 ± 0.3 | 1.1 | 5 | 2.777778 |
| 4i | 2.9 ± 0.2 | 1.6 | 7 | 2.413793 |
| 4l | 1.5 ± 0.5 | 0.9 | 3 | 2 |
| 4m | 2.5 ± 0.2 | 1.2 | 6 | 2.4 |
| 4n | 1.0 ± 0.2 | 0.6 | 2.5 | 2.5 |
| 4o | 2.5 ± 0.5 | 1.3 | 8 | 3.333333 |
| 4p | 1.5 ± 0.1 | 0.8 | 3 | 2 |
| Cisplatin | 5.0 ± 0.5 | 1.5 | 5 | 1 |

In the examples that follow, the broad spectrum active compound 4d was used for further analysis because its $IC_{50}\%$ was less than 4 g/ml and the selectivity index to the cancer cells was greater than 2.

Example 18

Colony Forming Assay

HCT-116 cells were seeded in 35 mm cell culture dish (500 cells/ml, 2 ml/dish). After overnight incubation at 37° C. and 5% $CO_2$, the medium was replaced with fresh medium containing either DMSO or 2 μM of 4d. The dishes were returned into the incubator and watched for the formation of single colonies. After 10 days, the experiment was stopped by washing the colonies by ice-cold 1×-PBS and fixed with ice-cold methanol. The colonies were left to air dry, then stained with 0.5% crystal violet. The excess stain was washed off by tap water. The colonies were counted by Gx microscopes (GXMGXD202 Inverted Microscope) (10× Eyepiece) and images were processed by ImageJ 1.47v. The effect of compound 4d on the colony formation of colon cancer cells was evaluated by incubating the cells with 1 μM. The resulting photomicrographic comparison showed that compound 4d was able to inhibit the formation of colonies in comparison to the control. This confirms the ability of compound 4d to enhance tumor suppressor activities.

Example 19

Wound-Healing Assay

HCT-116 cells were seeded in 6 well plate as 10*10⁴ cells per ml (2 ml in each well) and incubated overnight at 37° C. and 5% $CO_2$. On the second day, a scratch was created in each well by using a sterile P200 tip, and then the medium was replaced with fresh medium containing either DMSO or 1 μM of compound 4d. Photomicrograph images were taken at different time points (0, 4, 24 and 48 hours) to monitor the wound closure. After that, the cells were washed two times with ice-cold 1×PBS and fixed with ice-cold methanol for 20 min at 4° C. The fixed cells were washed two times with 1×PBS and stained with 0.5% crystal violet for 30 min. The extra stain was washed off by $dH_2O$ until no color in the washing is observed. The images were captured by Gx microscopes (GXMGXD202 Inverted Microscope) (10× Eyepiece) after staining with crystal violet. The size of the wound was measured by using ImageJ 1.47v software. Photomicrographs showed that the cells in the untreated "wound" approximated each other to attempt wound closure, while the cells treated with compound 4d remained separated at the scratch, showing that compound 4d inhibited wound closure. This confirms the ability of compound 4d to enhance tumor suppressor activities.

Example 20

Cell Cycle Analysis

Figure 3A:
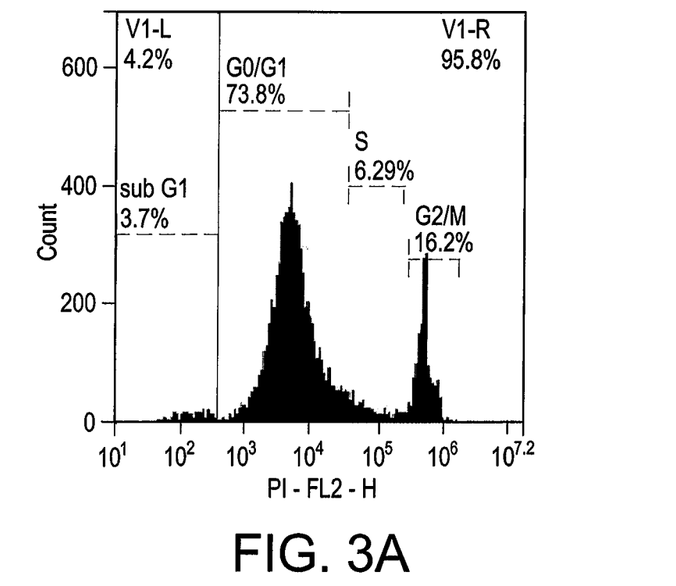
FIG. 3A is a flow cytometry plot showing a cell cycle analysis of untreated colon cancer cells incubated for 24 hours, then stained with propidium iodide.
Figure 3B:
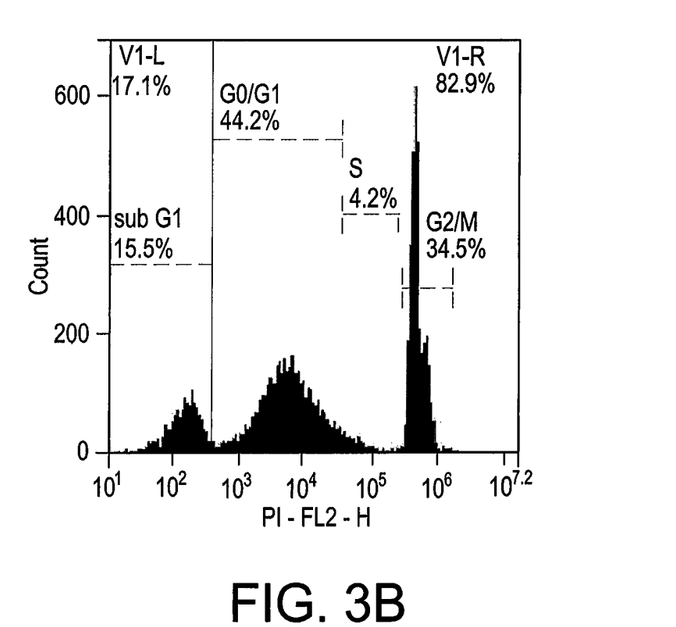
FIG. 3B is a flow cytometry plot showing a cell cycle analysis of colon cancer cells treated with 2 µM of compound 4d for 15 minutes and incubated for 24 hours, then stained with propidium iodide.

The cells (HCT-116) were seeded $5*10^4$ cells/mL in a 6-well plate (2 mL/well) and allowed to adhere overnight at 37° C. and 5% $CO_2$. The cells were incubated with or without 2 μM of compound 4d for 24 hours. The cells were washed twice with ice-cold 1×PBS and collected after trypsinzation. The cell pellet was washed two times with ice-cold 1×PBS and fixed with ice-cold 70% ethanol overnight at −20° C. After that, the cells were washed once with ice-cold PBS and the second wash was done with ice-cold PBS-2% FBS. The cell pellet was re-suspended in 500 μL Propidium Iodide (PI)/RNase (BD Biosciences, BDB550825) staining solution for 15 min at room temperature. The samples were incubated for 15 min in the dark and analyzed within 1 hour by BD Accuri™ C6 Plus flow cytometer. Cell cycle analysis after treating colon cancer cells with 2 μM of compound 4d revealed that compound 4d arrested around 34.5% and 15.5% of cells in G2/M and subG1, respectively (see FIG. 3B, as compared to the untreated cells in FIG. 3A). The arrest of the cell cycle in subG1 indicates the induction of apoptosis.

Example 21

Induction of Apoptosis

Figure 4A:
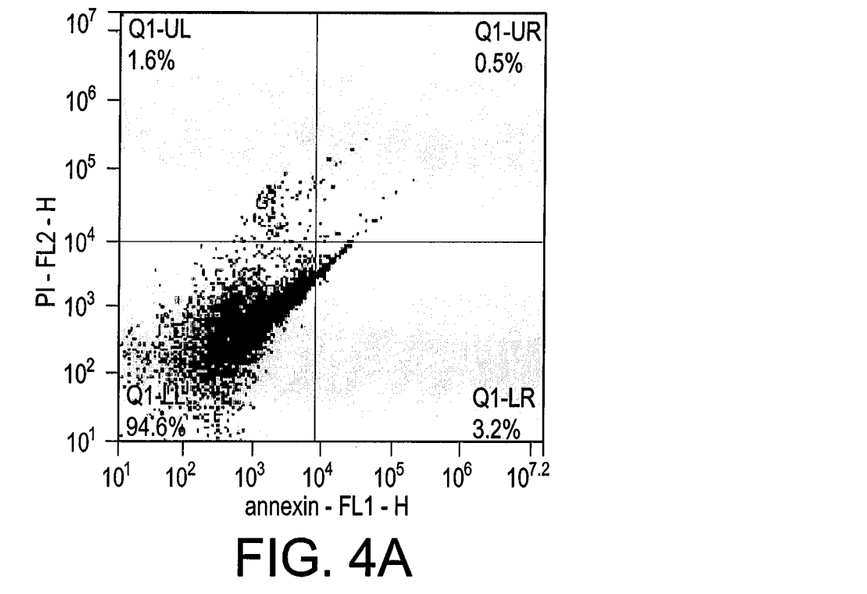
FIG. 4A is a flow cytometry plot showing a cell cycle analysis for apoptotic stage testing of untreated colon cancer cells incubated for 48 hours, then stained with propidium iodide and a fluorescent Annexin V antibody.
Figure 4B:
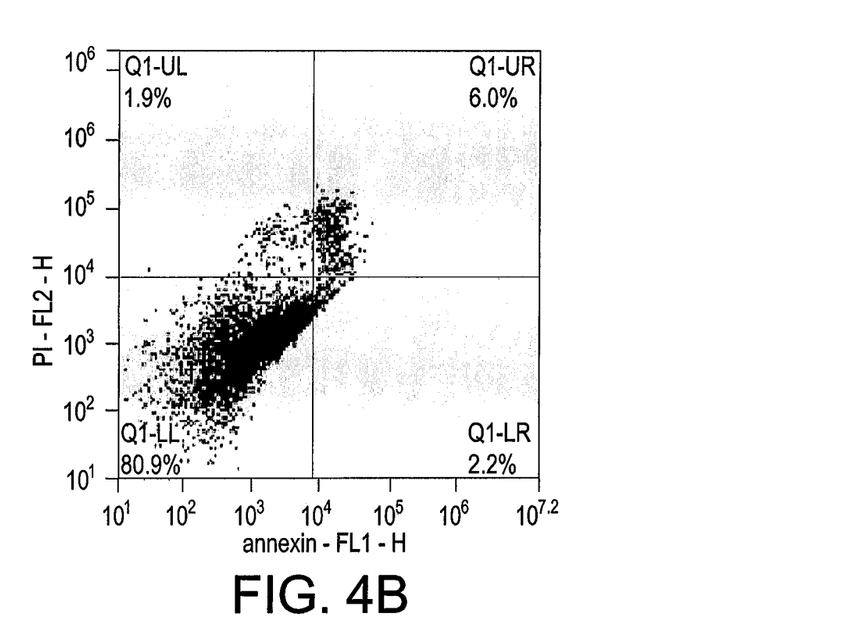
FIG. 4B is a flow cytometry plot showing a cell cycle analysis for apoptotic stage testing of colon cancer cells treated with 2 µM of compound 4d for 15 minutes and incubated for 48 hours, then stained with propidium iodide and a fluorescent Annexin V antibody.
Figure 5A:
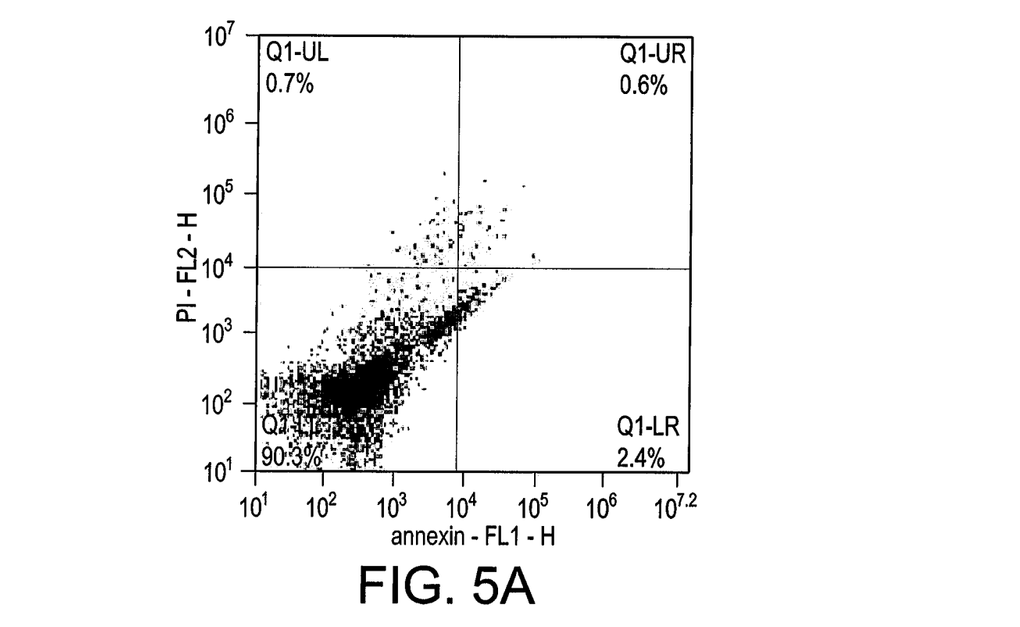
FIG. 5A is a flow cytometry plot showing a cell cycle analysis for apoptotic stage testing of untreated colon cancer cells incubated for 24 hours, then stained with propidium iodide and a fluorescent Annexin V antibody.
Figure 5B:
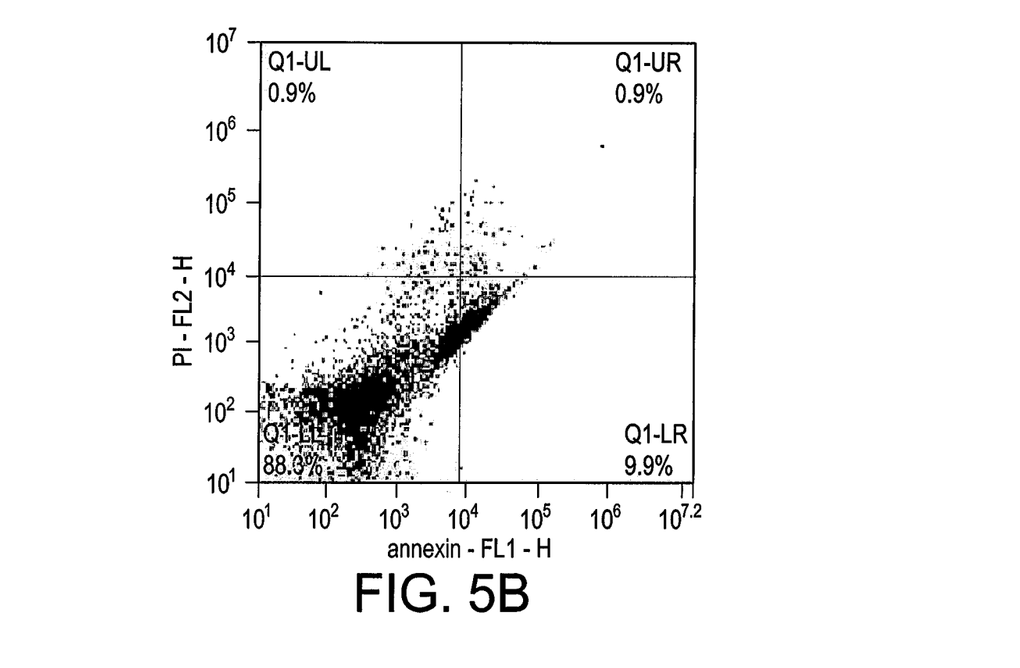
FIG. 5B is a flow cytometry plot showing a cell cycle analysis for apoptotic stage testing of colon cancer cells treated with 1 µM of compound 4d for 15 minutes and incubated for 24 hours, then stained with propidium iodide and a fluorescent Annexin V antibody.

The HCT-116 cells were seeded at $5*10^4$ cells/mL density in a 6-well plate. The cells were treated with 2 μM 4d for 48 hrs, and the cells were collected after trypsin enzyme treatment and washed two times with ice-cold 1×PBS. The cells were incubated for 2 hours at 4° C. in PBS, then centrifuged and re-suspended in 1× binding buffer. Then 5 μL PE annexin-V and 5 μL 7-amino-actinomycin D (7-AAD) were added to 100 μL of cell suspension and incubated for 15 min at RT in the dark, and then 400 μL of 1× binding buffer was added to the cell suspension and analyzed within 1 hour by BD Accuri™ C6 Plus flow cytometer. The following controls were used to set up the machine: cells unstained with PE annexin V and 7-AAD, cells stained with PE annexin V only, cells stained with 7-AAD only. The level of apoptotic cells, whether in early (+ve annexin-V and −ve PI) or late stage (+ve Annexin-V and +ve PI), was determined. As shown in FIG. 4B (as compared to the untreated cells in FIG. 4A), 2 μM of compound 4d for 48 hours treatment greatly increased the apoptotic cells. Because 2 days treatment did not show cells in the early stage of apoptosis, we repeated the experiment with short treatment time (24 hours) and with just 1 μM of compound 4d. The results are shown in FIG. 5A (untreated cells) and FIG. 5B (treated with just 1 μM of compound 4d for 24 hours). We found that even the short treatment time and lower concentration could induce the apoptosis.

Example 22

Molecular Docking Studies

A library of reported active spirooxoindoles and one of our exemplary synthesized compounds (4d) was designed and energy minimized using MMFF94 force field calculations. The catalytic domain of MDM2 was obtained from protein data bank (PDB code: 5law) and was prepared for docking using Open Eye® software. Open Eye Omega application was used to generate different conformations of each ligand. Docking was conducted using Fred, and the data was visualized by Veda application. This software package generates consensus scoring, which is a filtering process to obtain virtual binding affinity. The lower the consensus score, the better binding affinity of the ligands towards the receptor. This study revealed that the standard spirooxindole (6SJ) interacts in the receptor active site with consensus score 41. It showed two hydrogen bonds (HB) towards the binding site of MDM coming from the —NH of the indole moiety and the oxygen of the hydroxyl group with Leu 54:A (1.64 Å) and with Lys 94:A (2.00 Å), respectively. This docking mode is similar to co-crystallized docking pose with receptor. Compound 4d docked with the same receptor with consensus score 91 through a hydrophobic-hydrophobic interaction towards the binding active site without formation of HB. However, our compound form same pose of interaction and overlay with standard ligand (6SJ) and other reported compounds in the receptor active site. This binding mode suggested that the presence of a substituted cinnamoyl fragment, namely, a 2,4-dichlorostyryl moiety, acts as an important arm, and we can speculate it is a new pharmacophore.

Example 23 p53 Activation Studies

Figure 6A:
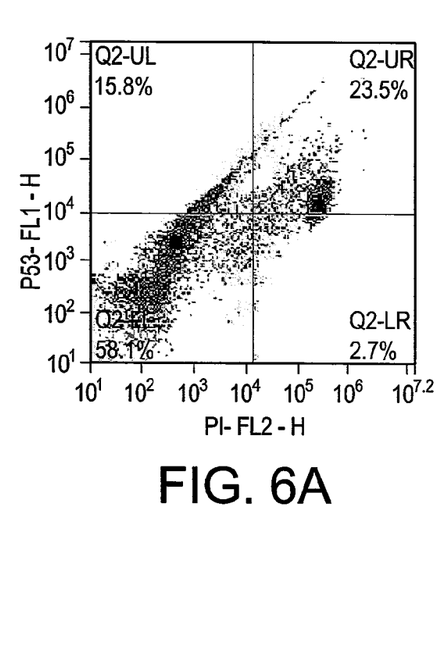
FIG. 6A is a flow cytometry plot showing a cell cycle analysis for apoptotic stage testing of untreated HCT-116 cancer cells incubated for 1 hour with a fluorescent p53 antibody, then stained with propidium iodide.
Figure 6B:
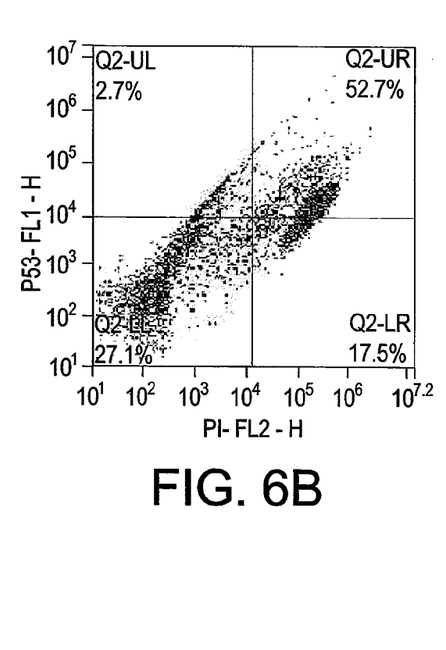
FIG. 6B is a flow cytometry plot showing a cell cycle analysis for apoptotic stage testing of HCT-116 cancer cells treated with 1 µM of compound 4d and incubated for 1 hour with a fluorescent p53 antibody, then stained with propidium iodide.
Figure 6C:
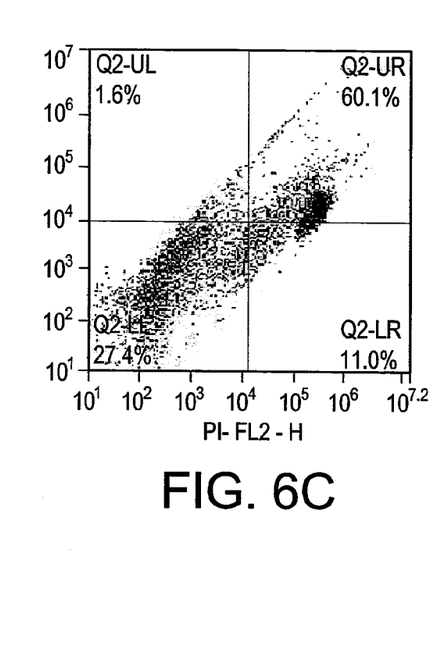
FIG. 6C is a flow cytometry plot showing a cell cycle analysis for apoptotic stage testing of HCT-116 cancer cells treated with 2 µM of compound 4d and incubated for 1 hour with a fluorescent p53 antibody, then stained with propidium iodide.

The determination of p53 protein level by flow cytometry was applied because it measures the level in a single cell and determines the heterogeneity of expression within a population of cells. HCT-116 (wt p53) cells were seeded at $5*10^4$ cells/mL density in a 6-well plate (2 ml/well). The cells were treated with 1 or 2 μM of compound 4d for 48 hrs, and the cells were collected after trypsin enzyme treatment and washed two times with ice-cold 1×PBS. The cells were fixed with 4% paraformaldehyde for fixation and permeabilization, then washed one time with 1× ice-cold PBS and one time with PBS containing 2% FBS. Then an aliquot of the cells was incubated with an anti-p53 antibody for one hour, and then washed two times with PBS. After that, the same cells were stained with PI (propidium iodide). The molecular docking study for compound 4d was found to interact (see Example 22). In order to confirm the effect of compound 4d on the activation of p53, we incubated the colon cancer cells with 2 μM of compound 4d, and after 24 hours, the cells were stained with the antibody against p53. We observed a significant increase in the cell population that was positive for p53. See FIGS. 6B (1 μM treatment with compound 4d for 48 hours; 52.7% shift in fluorescence) and 6C (2 μM treatment with compound 4d for 48 hours; 60.1% shift in fluorescence) compared to FIG. 6A (untreated cancer cells; 23% shift in fluorescence).

In summary, we have succeeded to generate potent anticancer derivatives through MDM2-p53 PPI inhibitors. Our studies provide a convincing example that a structure-based strategy can be employed to design small-molecule, non-peptide, highly potent inhibitors to target protein-protein interaction, which remains a very challenging area in chemical biology and drug design. Further optimization of this class of promising MDM2 inhibitors may ultimately lead to the development of an entirely new type of anticancer drug. Judging from the docking study, the installation of a multiply fused ring system containing a styryl (or benzylidine) part allowed the precise positioning of functional groups for π-π interactions, leading to the above compounds.

It is to be understood that the present invention is not limited to the embodiments described above, but encompasses any and all embodiments within the scope of the following claims.

We claim:

1. A substituted spirooxindole for cancer treatment, comprising a compound having the formula:

wherein $R_1$ and $R_4$ are independently hydrogen or chlorine; $R_2$ is hydrogen, chlorine, fluorine bromine, trifluoromethyl, methyl, or methoxy; $R_3$ is hydrogen, nitro ($NO_2$), fluorine, or bromine; and $R_5$ is hydrogen, chlorine, or bromine.

2. A substituted spirooxindole for cancer treatment, comprising a compound having the formula:

wherein X is sulfur or oxygen.

3. A substituted spirooxindole for cancer treatment, comprising a compound having the formula:

* * * * *